United States Patent
Magnus et al.

(10) Patent No.: US 6,770,763 B2
(45) Date of Patent: Aug. 3, 2004

(54) ASYMMETRIC SYNTHESIS OF AMINO-PYRROLIDINONES

(75) Inventors: Nicholas A. Magnus, Indianapolis, IN (US); Pasquale N. Confalone, Greenville, DE (US); Scott A. Savage, Yardley, PA (US); Matthew Yates, Lafayette, IN (US); Robert E. Waltermir, Hillsborough, NJ (US); David J. Meloni, Bear, DE (US); Silvio Campagna, Candia, NH (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/389,528

(22) Filed: Mar. 14, 2003

(65) Prior Publication Data

US 2003/0236401 A1 Dec. 25, 2003

Related U.S. Application Data

(60) Provisional application No. 60/387,637, filed on Jun. 11, 2002.

(51) Int. Cl.[7] .............................................. C07D 207/04
(52) U.S. Cl. ...................... 548/550; 548/551; 502/333; 546/248.4
(58) Field of Search ................................ 548/550, 551; 546/278.4; 502/333

(56) References Cited

U.S. PATENT DOCUMENTS

| 4,428,938 A | 1/1984 | Kisfaludy et al. |
| 6,057,336 A | 5/2000 | Duan et al. |

FOREIGN PATENT DOCUMENTS

| WO | WO 98/44797 | 10/1998 |
| WO | WO 02/04416 | 1/2002 |

*Primary Examiner*—Ceila Chang
*Assistant Examiner*—Golam M M Shameem
(74) *Attorney, Agent, or Firm*—David H. Vance; Jing S. Belfield

(57) ABSTRACT

A novel process for the asymmetric synthesis of an amino-pyrrolidinone of the type shown below from appropriate pyrrolidinones is described.

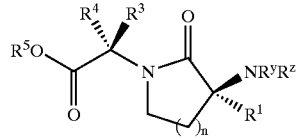

These compounds are useful as intermediates for MMP and TACE inhibitors.

12 Claims, No Drawings

ASYMMETRIC SYNTHESIS OF AMINO-PYRROLIDINONES

CROSS-REFERENCE TO RELATED APPLICATIONS

This application claims the priority benefit of U.S. Provisional Application No. 60/387,637, filed Jun. 11, 2002, the disclosure of which is incorporated herein by reference in its entirety.

FIELD OF THE INVENTION

The present invention relates generally to processes for the asymmetric synthesis of amino-pyrrolidinones, such pyrrolidinones being useful as intermediates for MMP and TACE inhibitors.

BACKGROUND OF THE INVENTION

Amino-pyrrolidinones of the type shown below are currently being studied as MMP and TACE inhibitors in clinical settings. As one of ordinary skill in the art understands, clinical trials and NDA submissions require practical, large-scale synthesis of the active drug.

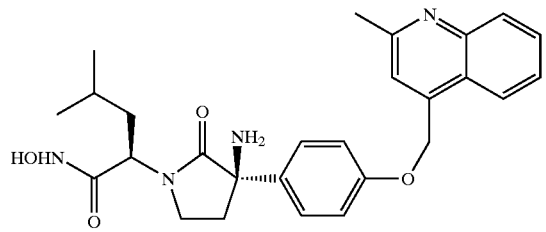

Consequently, it is desirable to find new synthetic procedures for making amino-pyrrolidinones.

SUMMARY OF THE INVENTION

Accordingly, the present invention provides a novel intermediate for making an amino-pyrrolidinone.

The present invention provides a novel amino-pyrrolidinone.

The present invention provides a novel process for making amino-pyrrolidinones.

These and other objects, which will become apparent during the following detailed description, have been achieved by the inventors' discovery that novel compounds of formula II can be formed from novel compounds of formula I.

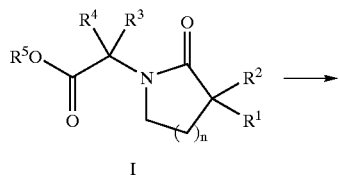

I

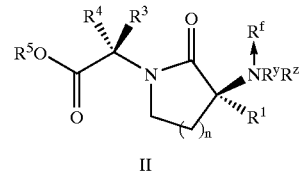

II

DETAILED DESCRIPTION OF THE INVENTION

Thus, in an embodiment, the present invention provides a novel process of forming a compound of formula II, comprising:

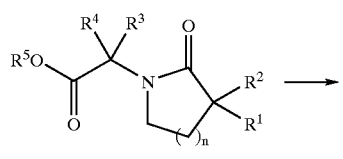

I

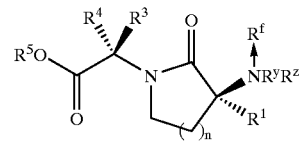

II (a) contacting a compound of formula I with a strong base in the presence of a first solvent, wherein the first solvent is an aprotic solvent;

(b) contacting the resulting solution from (a) with an aminating reagent, wherein the aminating reagent is an electrophilic nitrogen source; and, (c) if necessary, treating the amination product of (b) by reducing, hydrolyzing, or a combination thereof to form a compound of formula II;

wherein:

$R^f$ is absent;

$R^y$ is selected from H, OH, $C_{1-6}$ alkyl, and $C_{3-12}$ cycloalkyl;

$R^z$ is selected from H, $C_{1-6}$ alkyl, and $C_{3-12}$ cycloalkyl;

alternatively, $R^f$ is O, $R^z$ is absent, and $R^y$ forms a $C_{3-12}$ cycloalkyl group double bonded to the nitrone nitrogen or is a carbon atom double bonded to the nitrone nitrogen and substituted with $R^6$ and $R^7$;

$R^6$ is $C_{1-6}$ alkyl or $C_{3-12}$ cycloalkyl;

$R^7$ is $C_{1-6}$ alkyl or $C_{3-12}$ cycloalkyl;

$R^1$ is $Z—U^a—X^a—Y^a—Z^a$;

Z is phenyl or pyridyl substituted with 1–5 $R^b$;

$U^a$ is absent or is selected from O and $NR^a$;

$X^a$ is absent or is selected from $C_{1-10}$ alkylene, $C_{2-10}$ alkenylene, and $C_{2-10}$ alkynylene;

$Y^a$ is absent or is selected from O and $NR^a$;

$Z^a$ is selected from H, $C_{3-13}$ carbocyclic residue substituted with 0–5 $R^c$, and a 5–14 membered heterocyclic system containing from 1–4 heteroatoms selected from the group consisting of N, O, and S, and substituted with 0–5 $R^c$;

$R^2$ is H;

$R^3$ is selected from H, Q, $C_{1-10}$ alkylene-Q, $C_{2-10}$ alkenylene-Q, $C_{2-10}$ alkynylene-Q, $(CRR^x)_{r1}$ $O(CRR^x)_r$—Q, and $(CRR^x)_{r1}NR^a(CRR^x)_r$—Q;

Q is selected from H and a $C_{3-13}$ carbocyclic residue substituted with 0–5 $R^d$;

R, at each occurrence, is independently selected from H, $CH_3$, $CH_2CH_3$, $CH=CH_2$, $CH=CHCH_3$, and $CH_2CH=CH_2$;

$R^x$, at each occurrence, is independently selected from H, $CH_3$, $CH_2CH_3$, and $CH(CH_3)_2$;

$R^4$ is selected from H, $C_{1-10}$ alkylene-H, $C_{2-10}$ alkenylene-H, $C_{2-10}$ alkynylene-H, $(CRR^x)_{r1}O(CRR^x)_r$—H, and $(CRR^x)_{r1}NR^a(CRR^x)_r$—H;

alternatively, $R^3$ and $R^4$ combine to form a $C_{3-13}$ carbocyclic residue substituted with $R^{4a}$ and 0–3 $R^b$;

$R^{4a}$ is $U^a$—$X^a$—$Y^a$—$Z^a$;

$R^5$ is selected from H, $C_{1-6}$ alkyl, phenyl, and benzyl;

$R^a$, at each occurrence, is independently selected from H, $C_{1-4}$ alkyl, phenyl, and benzyl;

$R^{a1}$, at each occurrence, is independently selected from H, $C_{1-4}$ alkyl, phenyl, and benzyl;

$R^{a2}$, at each occurrence, is independently selected from H, $C_{1-4}$ alkyl, benzyl, $C_{3-7}$ carbocyclic residue, and a 5 to 6 membered heteroaromatic ring containing 1–4 heteroatoms selected from the group consisting of N, O, and S;

alternatively, $R^a$ and $R^{a1}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, CN, $NR^aR^{a1}$, $S(O)_2NR^aR^{a1}$, $CF_3$, and $CF_2CF_3$;

$R^c$, at each occurrence, is independently selected from $C_{1-6}$ alkyl, $OR^a$, F, $NR^aR^{a1}$, $CF_3$, and $CF_2CF_3$;

$R^d$, at each occurrence, is independently selected from $C_{1-6}$ alkyl, $OR^a$, F, $NR^aR^{a1}$, $S(O)_2NR^aR^{a1}$, $CF_3$, and $CF_2CF_3$;

n is selected from 0, 1, 2, and 3;

r, at each occurrence, is selected from 0, 1, 2, 3, 4, and 5; and, r1, at each occurrence, is selected from 0, 1, 2, 3, 4, and 5.

In a preferred embodiment, the present invention provides a novel process, wherein (c) is performed by reducing the amination product from (b) to form a compound of formula II, wherein:

$R^y$ is selected from H, $C_{1-6}$ alkyl, and $C_{3-12}$ cycloalkyl; and, $R^z$ is selected from H, $C_{1-6}$ alkyl, and $C_{3-12}$ cycloalkyl.

In another preferred embodiment, the present invention provides a novel process, wherein (a) is performed in the presence of an inorganic salt selected from a lithium salt, a potassium salt, and a sodium salt; and (c) is performed by contacting the amination product from (b) with a reducing agent and an acid;

the compound of formula I is the compound of formula Ia:

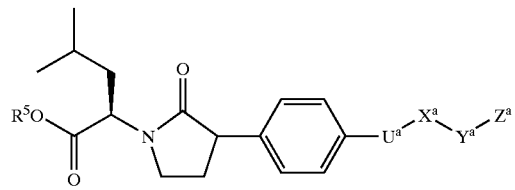

Ia the compound of formula II is a compound of formula IIa:

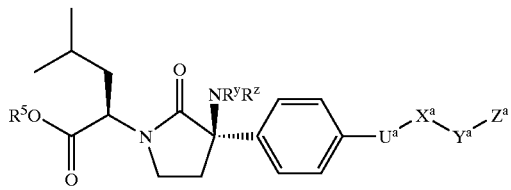

IIa the strong base is selected from an alkyl lithium, lithium amide, hydride base, and an organometallic base;

the first solvent is selected from an ethereal solvent, a hydrocarbon solvent, and an aromatic hydrocarbon solvent;

the aminating reagent is selected from a chloro-nitroso compound, a sulfonyl azide, a nitroso compound, an azodicarboxylate, a sulfonamide, and an oxaziridine compound;

the reducing agent is selected from zinc and iron;

the acid is selected from formic acid, acetic acid, and methanesulfonic acid;

wherein:

$R^y$ is H;

$R^z$ is H;

$U^a$ is absent or is O;

$X^a$ is absent or is $C_{1-4}$ alkylene;

$Y^a$ is absent;

$Z^a$ is selected from H, $C_{5-6}$ carbocyclic residue substituted with 0–2 $R^c$, and a 5–10 membered aromatic heterocyclic system containing from 1–4 heteroatoms selected from the group consisting of N, O, and S, and substituted with 0–2 $R^c$; and, $R^b$, at each occurrence, is independently selected from $C_{1-4}$ alkyl, $OR^a$, Cl, F, $NR^aR^{a1}$, and $CF_3$;

$R^c$, at each occurrence, is independently selected from $C_{1-4}$ alkyl, $OR^a$, F, $NR^aR^{a1}$, and $CF_3$; and, $R^5$ is H or $C_{1-6}$ alkyl.

In another preferred embodiment, the present invention provides a novel process, wherein (b) is performed in the presence of a second solvent and the second solvent is an aprotic solvent;

the inorganic salt is selected from lithium chloride, lithium perchlorate, lithium bromide, lithium iodide, potassium chloride, potassium bromide, potassium iodide, sodium chloride, sodium bromide, and sodium iodide;

the strong base is selected from methyl lithium, ethyl lithium, n-propyl lithium, i-propyl lithium, n-butyl lithium, i-butyl lithium, s-butyl lithium, t-butyl lithium, hexyl lithium, lithium bis(trimethylsilyl)amide, lithium diisopropylamide, lithium 2,2,6,6-tetramethylpiperidine, potassium bis(trimethylsilyl)amide, potassium hydride, and sodium hydride;

the first solvent is selected from tetrahydrofuran, 1,2-dimethoxyethane, t-butylmethyl ether, diethyl ether, and dimethoxymethane;

the second solvent is selected from tetrahydrofuran, 1,2-dimethoxyethane, t-butylmethyl ether, diethyl ether, dimethoxymethane, and toluene;

the aminating reagent is selected from 1-chloro-1-nitrosocyclopentane, 1-chloro-1-nitrosocyclohexane, and 2-chloro-2-nitrosopropane;

the reducing agent is zinc;

wherein:

$U^a$ is O;

$X^a$ is absent or is $CH_2$;

$Z^a$ is H or phenyl; and, $R^5$ is H or $CH_3$.

In another preferred embodiment, the present invention provides a novel process, wherein:

the inorganic salt is selected from lithium chloride and lithium perchlorate;

the strong base is selected from n-butyl lithium and hexyl lithium;

the first solvent is selected from tetrahydrofuran and 1,2-dimethoxyethane;

the second solvent is toluene; and, the aminating reagent is selected from 1-chloro-1-nitrosocyclopentane and 1-chloro-1-nitrosocyclohexane.

In another preferred embodiment, the present invention provides a novel process, wherein:

the inorganic salt is lithium chloride;

the strong base is n-butyl lithium;

the first solvent is tetrahydrofuran;

the second solvent is toluene;

the aminating reagent is 1-chloro-1-nitrosocyclopentane; and, the acid is formic acid.

In another preferred embodiment, the present invention provides a novel process, wherein (c) further comprises:

($c_1$) esterifying the acid product from $b_1$, wherein:
$R^5$ is $C_{1-6}$ alkyl.

In another preferred embodiment, the present invention provides a novel process, wherein in ($c_1$) the esterification is performed by contacting the reduced product with an acid in the presence of an alcohol.

In another preferred embodiment, the present invention provides a novel process, wherein the acid is methanesulfonic acid and the alcohol is methyl alcohol.

In another preferred embodiment, the present invention provides a novel process, further comprising:

(d) subjecting the compound from (c) wherein $R^y$ is OH to catalytic hydrogenation with a noble metal catalyst to form a compound of formula II wherein $R^y$ is H.

In another preferred embodiment, the present invention provides a novel process, wherein the noble metal catalyst is palladium.

In another embodiment, the present invention provides a novel compound of formula IIb:

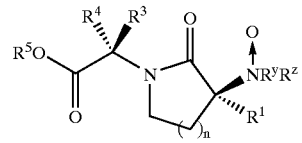

wherein:

$R^z$ is absent and $R^y$ forms a $C_{3-12}$ cycloalkyl group double bonded to the nitrone nitrogen or is a carbon atom double bonded to the nitrone nitrogen and substituted with $R^6$ and $R^7$;

$R^6$ is $C_{1-6}$ alkyl or $C_{3-12}$ cycloalkyl;

$R^7$ is $C_{1-6}$ alkyl or $C_{3-12}$ cycloalkyl;

$R^1$ is $Z-U^a-X^a-Y^a-Z^a$;

Z is phenyl or pyridyl substituted with 1–5 $R^b$;

$U^a$ is absent or is selected from O and $NR^a$;

$X^a$ is absent or is selected from $C_{1-10}$ alkylene, $C_{2-10}$ alkenylene, and $C_{2-10}$ alkynylene;

$Y^a$ is absent or is selected from O and $NR^a$;

$Z^a$ is selected from H, $C_{3-13}$ carbocyclic residue substituted with 0–5 $R^c$, and a 5–14 membered heterocyclic system containing from 1–4 heteroatoms selected from the group consisting of N, O, and S, and substituted with 0–5 $R^c$;

$R^2$ is H;

$R^3$ is selected from H, Q, $C_{1-10}$ alkylene-Q, $C_{2-10}$ alkenylene-Q, $C_{2-10}$ alkynylene-Q, $(CRR^x)_{r1}O(CRR^x)_r-Q$, and $(CRR^x)_{r1}NR^a(CRR^x)_r-Q$;

Q is selected from H and a $C_{3-13}$ carbocyclic residue substituted with 0–5 $R^d$;

R, at each occurrence, is independently selected from H, $CH_3$, $CH_2CH_3$, $CH=CH_2$, $CH=CHCH_3$, and $CH_2CH=CH_2$;

$R^x$, at each occurrence, is independently selected from H, $CH_3$, $CH_2CH_3$, and $CH(CH_3)_2$;

$R^4$ is selected from H, $C_{1-10}$ alkylene-H, $C_{2-10}$ alkenylene-H, $C_{2-10}$ alkynylene-H, $(CRR^x)_{r1}O(CRR^x)_r-H$, and $(CRR^x)_{r1}NR^a(CRR^x)_r-H$;

alternatively, $R^3$ and $R^4$ combine to form a $C_{3-13}$ carbocyclic residue substituted with $R^{4a}$ and 0–3 $R^b$;

$R^4a$ is $U^a-X^a-Y^a-Z^a$;

$R^5$ is selected from H, $C_{1-6}$ alkyl, phenyl, and benzyl;

$R^a$, at each occurrence, is independently selected from H, $C_{1-4}$ alkyl, phenyl, and benzyl;

$R^{a1}$, at each occurrence, is independently selected from H, $C_{1-4}$ alkyl, phenyl, and benzyl;

$R^{a2}$, at each occurrence, is independently selected from H, $C_{1-4}$ alkyl, benzyl, $C_{3-7}$ carbocyclic residue, and a 5 to 6 membered heteroaromatic ring containing 1–4 heteroatoms selected from the group consisting of N, O, and S;

alternatively, $R^a$ and $R^{a1}$ taken together with the nitrogen to which they are attached form a 5 or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, CN, $NR^aR^{a1}$, $S(O)_2NR^aR^{a1}$, $CF_3$, and $CF_2CF_3$;

$R^c$, at each occurrence, is independently selected from $C_{1-6}$ alkyl, $OR^a$, F, $NR^aR^{a1}$, $CF_3$, and $CF_2CF_3$;

$R^d$, at each occurrence, is independently selected from $C_{1-6}$ alkyl, $OR^a$, F, $NR^aR^{a1}$, $S(O)_2NR^aR^{a1}$, $CF_3$, and $CF_2CF_3$;

n is selected from 0, 1, 2, and 3;

r, at each occurrence, is selected from 0, 1, 2, 3, 4, and 5; and, r1, at each occurrence, is selected from 0, 1, 2, 3, 4, and 5.

In another preferred embodiment, the present invention provides a novel compound, wherein the compound is of formula IIc:

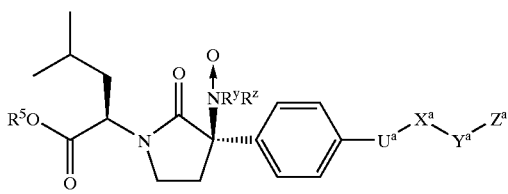

IIc wherein:

$R^z$ is absent and $R^y$ forms a cyclobutyl, cyclopentyl, or cyclohexyl group double bonded to the nitrone nitrogen;

$U^a$ is absent or is O;

$X^a$ is absent or is $C_{1-4}$ alkylene;

$Y^a$ is absent;

$Z^a$ is selected from H and phenyl; and, $R^5$ is H or $C_{1-6}$ alkyl.

In another preferred embodiment, the present invention provides a novel compound of formula IId:

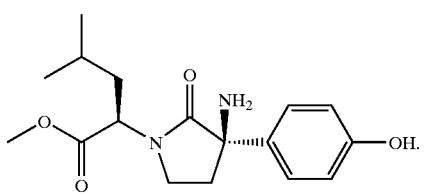

IId

In another preferred embodiment, the present invention provides a novel compound of the formula:

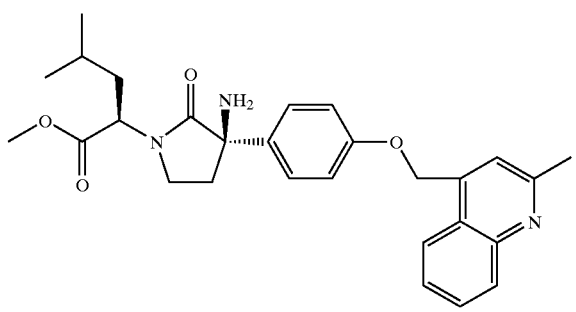

wherein the compound is present in its HCl salt form.

In another preferred embodiment, the present invention provides a novel compound of the formula:

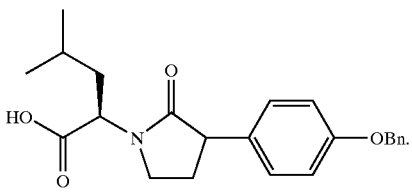

DEFINITIONS

The present invention can be practiced on multigram scale, kilogram scale, multikilogram scale, or industrial scale. Multigram scale, as used herein, is preferable in the scale wherein at least one starting material is present in 10 grams or more, more preferable at least 50 grams or more, even more preferably at least 100 grams or more. Multikilogram scale, as used herein, is intended to mean the scale wherein more than one kilo of at least one starting material is used. Industrial scale as used herein is intended to mean a scale which is other than a laboratory sale and which is sufficient to supply product sufficient for either clinical tests or distribution to consumers.

As used herein, the following terms and expressions have the indicated meanings. It will be appreciated that the compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, and racemic forms and all geometric isomeric forms of a structure are intended, unless the specific stereochemistry or isomer form is specifically indicated.

As used herein, equivalents are intended to mean molar equivalents unless otherwise specified.

The reactions of the synthetic methods claimed herein are carried out in suitable solvents which may be readily selected by one of skill in the art of organic synthesis, the suitable solvents generally being any solvent which is substantially non-reactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable polar solvents include, but are not limited to, ether and aprotic solvents.

Suitable ether solvents include: dimethoxymethane, tetrahydrofuran, 1,3-dioxane, 1,4-dioxane, furan, diethyl ether, 1,2-dimethoxyethane, diethoxymethane, dimethoxymethane, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable aprotic solvents may include, by way of example and without limitation, ether solvents, tetrahydrofuran (THF), dimethylformamide (DMF), 1,2-dimethoxyethane, diethoxymethane, dimethoxymethane, dimethylacetamide (DMAC), benzene, toluene, 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include, but are not limited to, benzene, cyclohexane, pentane, hexane, hexanes, toluene, cycloheptane, methylcyclohexane, heptane, ethylbenzene, m-xylene, o-xylene, p-xylene, octane, indane, nonane, or naphthalene.

As used herein, an alcohol solvent is a hydroxy-substituted compound that is liquid at the desired temperature (e.g., room temperature). Examples of alcohols include, but are not limited to, methyl alcohol, ethyl alcohol, n-propanol, and i-propanol.

As used herein, the term "amino protecting group" (or "N-protected") refers to any group known in the art of organic synthesis for the protection of amine groups. As used herein, the term "amino protecting group reagent" refers to any reagent known in the art of organic synthesis for the protection of amine groups that may be reacted with an amine to provide an amine protected with an amine-protecting group. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York, (1981), the disclosure of which is hereby incorporated by reference. Examples of amine protecting groups include, but are not limited to, the following: 1) acyl types such as formyl, trifluoroacetyl (TFA), phthalyl, and p-toluenesulfonyl; 2) aromatic carbamate types such as benzyloxycarbonyl (cbz) and substituted benzyloxycarbonyls, 2-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10,10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl) ethyloxycarbonyl; benzyloxycarbonyl; p-nitrobenzyloxycarbonyl; 2-(p-toluenesulfonyl) ethyloxycarbonyl; m-chloro-p-acyloxybenzyloxycarbonyl; 5-benzyisoxazolylmethyloxycrbonyl; p-(dihydroxyboryl) benzyloxycarbonyl; m-nitrophenyloxycarbonyl; o-nitrobenzyloxycarbonyl; 3,5-dimethoxybenzyloxycrbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; and methanesulfonamide.

As used herein, the term "noble metal catalyst" refers to noble metals, known in the art of organic synthesis, used in catalytic hydrogenation. Examples of noble metal catalysts include, but are not limited to, palladium or platinum.

Preferably, the molecular weight of compounds of the present invention is less than about 500, 550, 600, 650, 700, 750, 800, 850, 900, 950, or 1000 grams per mole. More preferably, the molecular weight is less than about 950 grams per mole. Even more preferably, the molecular weight is less than about 850 grams per mole. Still more preferably, the molecular weight is less than about 750 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

SYNTHESIS

By way of example and without limitation, the present invention may be further understood by the following schemes and descriptions. Scheme 1 exemplifies how a desired end product can be formed using the presently claimed process and intermediates.

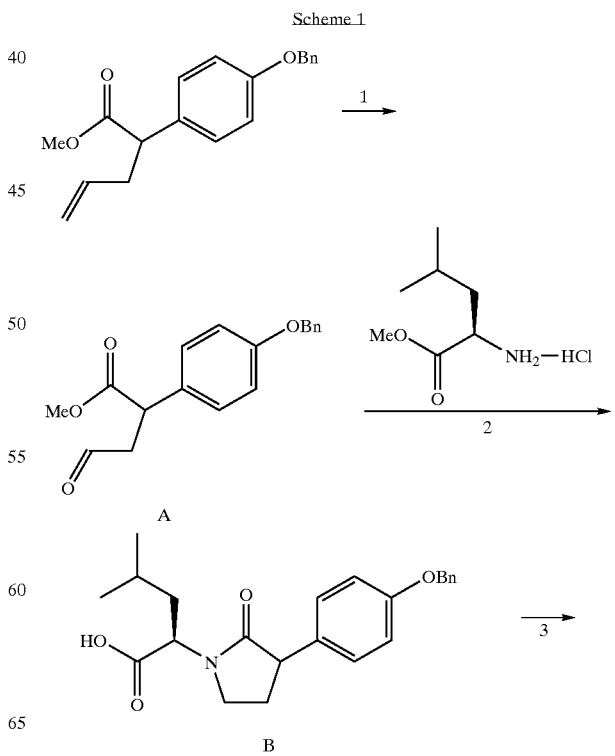

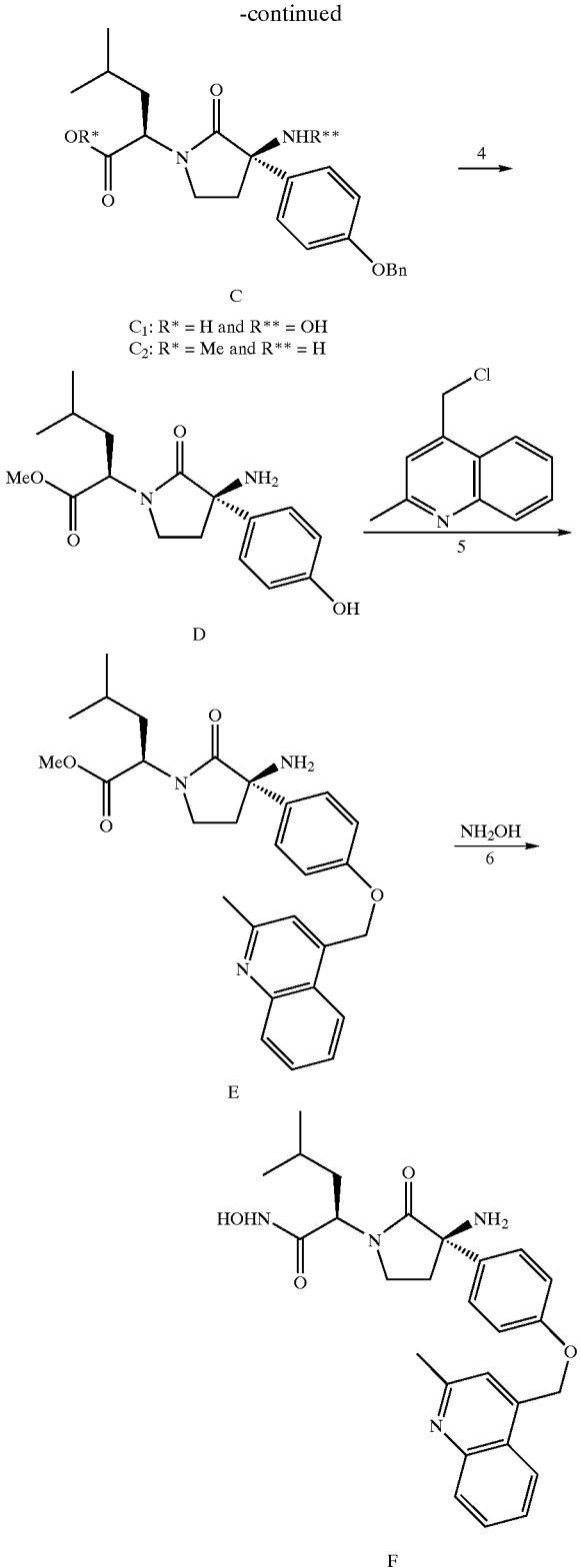

C

C₁: R* = H and R** = OH
C₂: R* = Me and R** = H

Starting Material: 2-(4-Benzyloxy-phenyl)-pent-4-enoic acid methyl ester can be prepared by alkylating 2-(4-benzyloxy-phenyl)-ethanoic acid methyl ester. The starting ester is deprotonated with a strong base and then alkylated with an allyl alkylating reagent. Preferably, the base is selected from lithium diisopropylamide, lithium hexamethyldisilamide, as well as other lithium bases. More preferably, the base is lithium diisopropylamide or lithium hexamethyldisilamide. Even more preferably, the base is lithium diisopropylamide. Preferably from 0–9 to 1.2 equivalents of base are used, more preferably 1.1. The allyl alkylating agent is preferably allyl bromide or allyl chloride, with allyl bromide being more preferred. Preferably, 0.9 to 2 equivalents of alkylating agent are use, more preferably 1.3. An aprotic solvent is preferably used. Preferred solvents include tetrahydrofuran, dimethylformamide, and diethoxymethane, with tetrahydrofuran being more preferred.

Reaction 1: Compound A can be formed by methods known to those of skill in the art of organic synthesis. For example, it can be formed by subjecting the shown compound to ozonolysis and then quenched. Preferably 1–2 equivalents of ozone are used, more preferably 1. Preferably, the ozonolysis is quenched with Zn. From 1–5 equivalents of Zn are preferred with 2 being more preferred. Generally, an acid is also used to quench the reaction. Preferably, the acid is acetic acid. Other work-ups include using dimethyl sulfide, triphenyl phosphine, and other phosphines known to those of ordinary skill in the art. Solvents including ethyl acetate and methylene chloride can be used. Ethyl acetate is preferred. Compound A need not be a benzyl-protected hydroxy-phenyl moiety. It could be one of numerous starting materials depending on the desired end product, Compound F.

Reaction 2: Lactam B can then be formed by methods known to those of skill in the art of organic synthesis. For example, compound A can be treated with a protected (e.g., methyl ester) amino acid under reductive amination conditions (e.g., NaBH(OAc)₃), cyclized to the lactam by heating, and the resulting product deprotected (e.g., LiOH). The protected amino acid used in this sequence will depend in the desired product. One of ordinary skill in the art would recognize that numerous different protected amino acids could be effectively used in this reaction.

Reaction 3: Reaction 3 generally involves two or three reactions: (a) deprotonating compound B, (b) contacting the resulting product with an aminating reagent, and, if desired, (c) converting the resulting intermediate to an amino group (Compound C₂) or a hydroxylamine (Compound C₁).

Reaction 3(a): Compound B is contacted with a strong base (e.g., n-BuLi) in the presence of a first solvent, wherein the first solvent is an aprotic solvent (e.g., THF). Preferably, the strong base is an alkyl lithium, lithium amide, hydride base, or other organometallic bases. More preferably, the strong base is methyl lithium, ethyl lithium, n-propyl lithium, i-propyl lithium, n-butyl lithium, i-butyl lithium, s-butyl lithium, t-butyl lithium, hexyl lithium, lithium bis(trimethylsilyl)amide, lithium diisopropylamide, lithium 2,2,6,6-tetramethylpiperidine, potassium bis(trimethylsilyl)amide, potassium hydride, or sodium hydride. Even more preferably, the strong base is n-butyl lithium or hexyl lithium. Still more preferably, the strong base is n-butyl lithium.

Preferably, the first solvent, an aprotic solvent, is an ethereal solvent, a hydrocarbon solvent, or an aromatic hydrocarbon solvent. More preferably, the first solvent is tetrahydrofuran, 1,2-dimethoxyethane, t-butylmethyl ether, diethyl ether, or dimethoxymethane. Even more preferably, the first solvent is tetrahydrofuran or 1,2-dimethoxyethane. Most preferably, the first solvent is tetrahydrofuran.

Reaction 3(a) is advantageously performed in the presence of an inorganic salt that is a lithium salt, a potassium salt, or a sodium salt. More preferably, the salt is lithium chloride, lithium perchlorate, lithium bromide, lithium iodide, potassium chloride, potassium bromide, potassium iodide, sodium chloride, sodium bromide, or sodium iodide. Even more preferably, the salt is lithium chloride or lithium perchlorate. Still more preferably, the salt is lithium chloride.

Reaction 3(b): Reaction 3(b) involves the addition of an a chiral aminating reagent diastereoselectively provide the tetra-substituted carbon. The resulting solution from (a) is contacted with an aminating reagent, wherein the aminating reagent is an electrophilic nitrogen source (e.g., 1-chloro-1-nitrosocyclopentane). Preferably, the aminating reagent is a chloro-nitroso compound, a sulfonyl azide, a nitroso compound, an azodicarboxylate, a sulfonamide, or an oxaziridine compound. More preferably, the aminating reagent is 1-chloro-1-nitrosocyclopentane, 1-chloro-1-nitrosocyclohexane, or 2-chloro-2-nitrosopropane. Even more preferably, the aminating reagent is 1-chloro-1-nitrosocyclopentane or 1-chloro-1-nitrosocyclohexane. Still more preferably, the aminating reagent is 1-chloro-1-nitrosocyclopentane.

Reaction 3(b) is preferably performed in the presence of a second solvent, preferably an aprotic solvent. More preferably, the second solvent is tetrahydrofuran, 1,2-dimethoxyethane, t-butylmethyl ether, diethyl ether, dimethoxymethane, benzene, and toluene. Even more preferably, the second solvent is benzene and toluene. Still more preferably, the second solvent is toluene.

The compound resulting from reaction 3(b) has two sterocenters. Preferably, the diastereoselectivity (i.e., de) is 10:1, more preferably 11:1, and even more preferably 13:1.

Reaction 3(c): After amination of Compound B, an aminated product is formed. In a preferred an embodiement the aminated product is a nitrone. The nitrone can be hydrolyzed to a hydroxylamine or reduced to an amino group depending on how it is treated. It is preferable to convert this nitrone to an amino group and esterify the acid group (Compound $C_2$).

The nitrone is reduced to an imine group by the addition of a reducing agent and concomitant hydrolysis and/or alcoholysis affords the amino group (e.g., zinc in the presence of an acid and an alcohol or water). A preferred reducing agent is zinc. Preferred acids used in conjunction with the reducing agent (i.e., zinc) include, but are not limited to, methanesulfonic acid, acetic acid, formic acid, hydrochloric acid, and sulfuric acid. A preferred combination is zinc and formic acid.

Esterification of the amino-acid resulting from nitrone reduction can be accomplished by methods known to those of ordinary skill in the art (i.e., addition of an acid and an alcohol). Esters that can be formed included, but are not limited to, methyl, ethyl, n-propyl, i-propyl, n-butyl, s-butyl, i-butyl, t-butyl, and benzyl. A preferred ester is an alkyl ester. A more preferred ester is methyl ester. Preferably, the methyl ester is formed by the addition of methyl alcohol and methanesulfonic acid. Other acids can be used, such as acetic acid, hydrochloric acid, and sulfuric acid.

The hydroxylamine group is generally obtained by treatment with water and an acid (e.g. methanesulfonic acid, citric acid, or formic acid). It is preferred to conduct this conversion in an alcoholic solvent (e.g., methyl alcohol). The hydroxylamine group can be converted to an amino group by methods known to those of ordinary skill in the art. For example, the hydroxylamine can be reduced to an amino group by the addition of a reducing agent (e.g., zinc in the presence of an acid). A preferred reducing agent is zinc. Preferred acids used in conjunction with the reducing agent (i.e., zinc) include, but are not limited to, methanesulfonic acid, acetic acid, formic acid, hydrochloric acid, and sulfuric acid. A preferred combination is zinc and formic acid.

Reaction 4: Reaction 4 depends on the desired end product, the protecting groups used, and the aminating reagent used. Certain selections of the end product, protecting groups, and aminating reagents can obviate the need for Reaction 4. As shown in Scheme 1, Reaction 4 involves deprotecting the hydroxyl group and, optionally, if the hydroxylamine is present, simultaneously converting it to an amine. The hydroxyl group can be deprotected and the hydroxylamine, if present, simultaneously converted to the amine by methods known to those of ordinary skill in the art. For example, the benzyl group can be removed and the hydroxylamine, if present, can be simultaneously converted to the amine by hydrogenation in the presence of a catalyst (e.g., Pd/C) and a solvent (e.g., methyl alcohol).

Reaction 5: Reaction 5 will depend on the desired end product as well as the protecting groups and aminating agents previously used. As shown in Scheme 1, Reaction 5 can involve treating compound D with a molecule having an appropriate leaving group (e.g., 4-chloromethyl-2-methyl-quinoline). It may also be useful to protect the free amine. For example, Compound D can be treated with an amine protecting agent (e.g., p-tolualdehyde under water removing conditions) and the resulting imine then treated with a molecule having an appropriate leaving group.

Compound E is preferably isolated as a salt. Preferred salts of E include methanesulfonic acid and hydrochloric acid. The hydrochloric acid salt is more preferred.

Reaction 6: Reaction 6 involves replacing the methoxy group with a hydroxylamine group. Suitable hydroxylamines include hydroxylamine hydrochloride and hydroxylamine sulfate. Preferably, hydroxylamine hydrochloride is used. From 1–10 equivalents of hydroxylamine are preferably used. More preferably, 5 equivalents of hydroxylamine are used. Alcohols such as methyl alcohol, t-amyl alcohol, and t-butyl alcohol can be used, methyl alcohol being preferred.

Examples of electrophilic nitrogen sources:

1) Nitrenoids of the type MRN—OR' (M=metal):

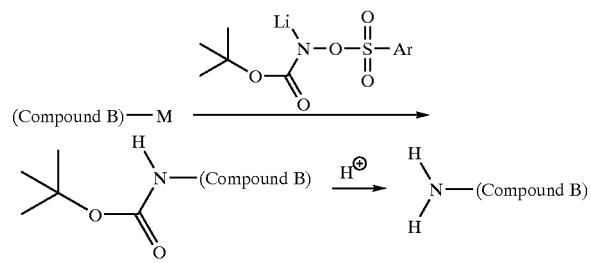

2) Azocarboxylates of the type $RCO_2N=NCO_2R$:

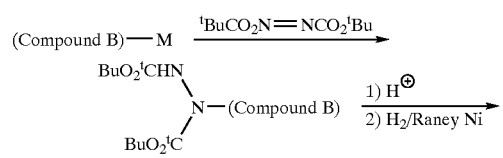

3) Sulfonylazides of the type RSO$_2$N$_3$:

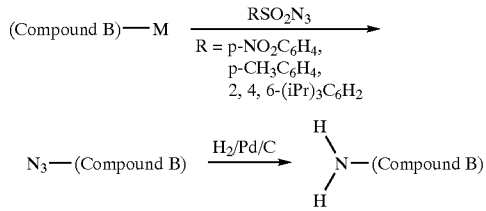

4) Oxaziridines of the type RCONR$^1$:

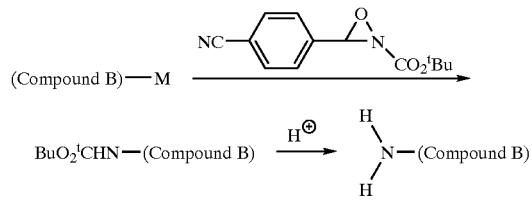

Alternative methods of making the lactam cores of the present invention are shown below.

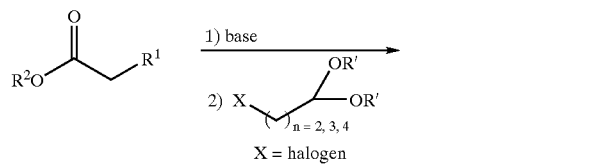

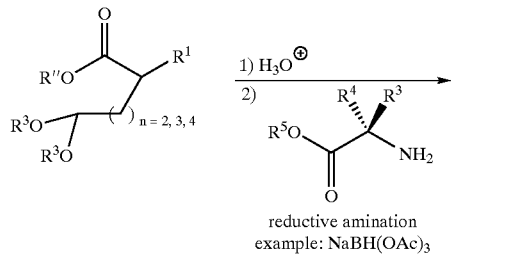

reductive amination
example: NaBH(OAc)$_3$

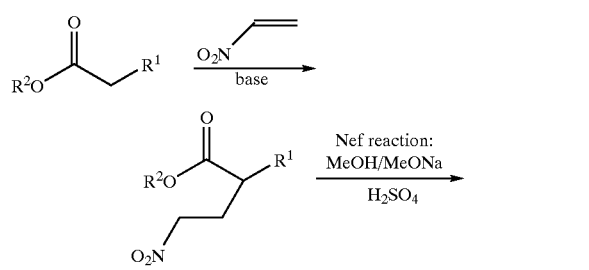

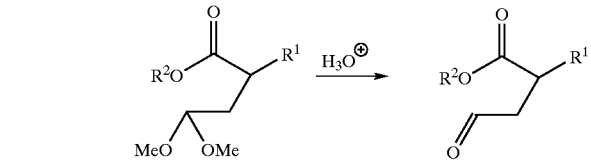

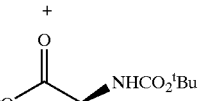

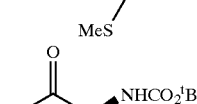

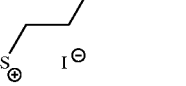

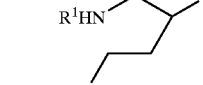

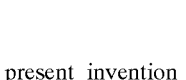

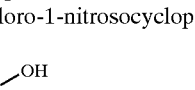

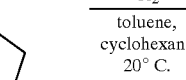

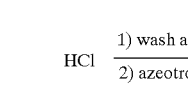

The present invention also includes the novel use of a 1-chloro-1-nitrosocyclopentane solution.

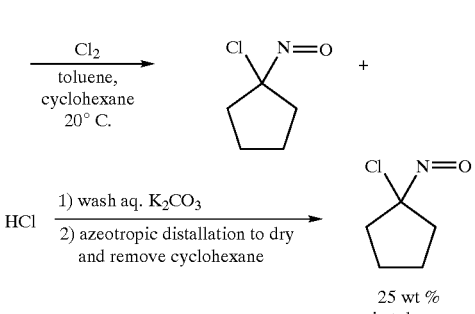

Reagents for preparing chloronitroso reagents: Cl$_2$, nitrosyl chloride (PhSO$_2$NCl$_2$), alkyl-hypochlorite ($^t$BuOCl), aqueous hypochlorous acid, hypochlorous acid/(1R)-isobornyl ester, NOCl, and N,N'-dichloro-N,N'-dinitro-ethylenediamine.

Solvents for preparing chloronitroso reagents: diethyl ether, benzene, cyclohexane, water, acetic acid, concentrated hydrochloric acid, toluene and ethyl acetate or similar solvents or mixtures thereof.

Halogenated solvents include: CCl$_3$F, CH$_2$Cl$_2$, CHCl$_3$, CCl$_4$.

Other features of the invention will become apparent in the course of the following descriptions of examplary embodiments which are given for illustration of the invention and are not intended to be limiting thereof.

EXAMPLES

Example 1

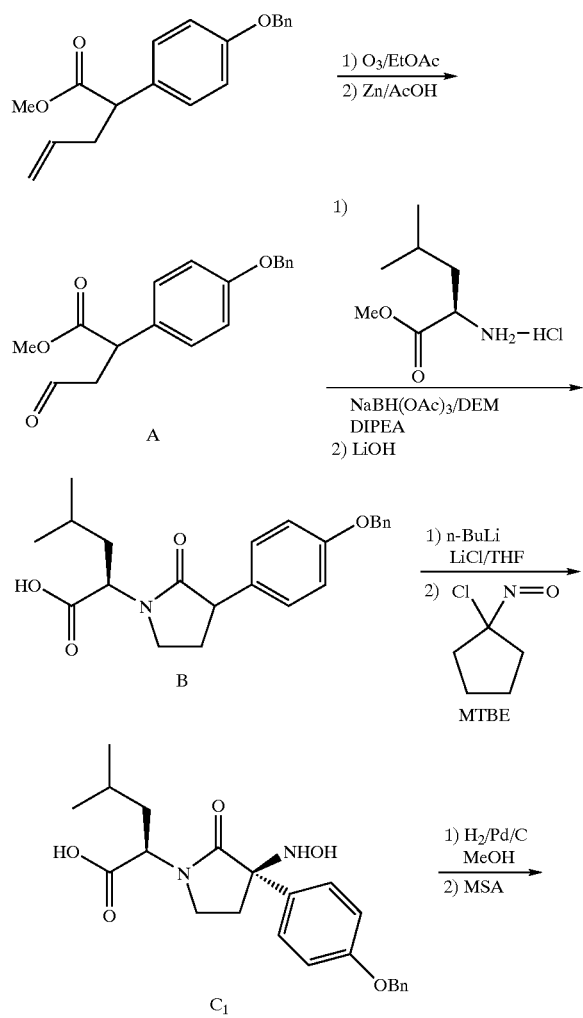

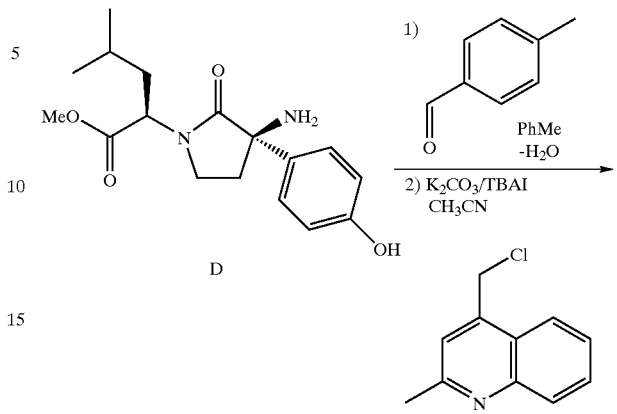

Compound A: 2-(4-benzyloxy-phenyl)-4-oxo-butyric acid methyl ester.

Under a nitrogen atmosphere, 2-(4-benzyloxy-phenyl)-pent-4-enoic acid methyl ester (750 g; 2.53 mol) is dissolved in ethyl acetate (7.5 L), and the resulting mixture cooled to −70° C. Ozone is introduced subsurface into the reaction for 3 h causing the reaction mixture to turn blue. The reaction mass is purged subsurface with nitrogen for 0.5 h to displace any residual ozone. At this point HPLC analysis indicates complete consumption of the starting material. The reaction mixture is warmed to −30° C. and held. In a separate vessel, zinc (450 g; 6.88 mol) and aqueous acetic acid (500 mL in 500 mL water) are combined and cooled to 0° C. The contents of the ozonolysis reactor are added to the aqueous acidic zinc mixture at such a rate as to maintain a reaction temperature of ≦0° C. After the addition is complete and the mixture has been held for 2 h, HPLC indicates conversion of intermediates to the desired aldehyde. The reaction mixture is filtered through Celite®, washed with water (2×4.5 L), and water (4.5 L) is added to the organic phase. Sodium bicarbonate (150 g; 1.79 mol) is added to the mixture, and stirring for 0.25 h gives a pH of >7. The aqueous layer is removed, and the volume is reduced to 2.25 L by reduced pressure distillation. The mixture is held at 50° C., and heptane (3L) is added to slowly provide a precipitate. The resulting slurry is cooled to 20° C. over 2 h, the solids are filtered, washed with heptane (3 L), and dried to constant weight at 45° C. and ~25" Hg. The title aldehyde, compound A (513 g; 68% isolated yield) is afforded as a tan solid.

IR (KBr pellet) 3441, 2952, 2833, 2727, 1729 cm$^{-1}$. $^1$H NMR (400 MHz, CDCl$_3$) δ 9.79 (1H, s), 7.46–7.34 (5H, m), 7.22 (2H, d, J=8.8 Hz), 6.96 (2H, d, J=8.8 Hz), 5.07 (2H, s), 4.11 (1H, dd, J=5.0, 9.6 Hz), 3.69 (3H, s), 3.39 (1H, dd, J=9.6, 18.7 Hz), 2.81 (1H, dd, J=5.0, 18.7 Hz). $^{13}$C NMR (100 MHz, CDCl$_3$) δ 199.6, 173.4, 158.1, 136.7, 129.8, 128.7, 128.5, 127.9, 127.3, 115.0, 69.8, 52.2, 47.2, 43.8. HRMS (ESI) calcd for C$_{18}$ H$_{19}$ O$_4$ (M$^+$) 299.128, found 299.128.

Compound B: 1-((R)-2-amino-4-methyl-pentanoic acid)-3-(4-benzyloxy-phenyl)-pyrrolidin-2-one.

Under a nitrogen atmosphere, compound A (1.00 kg; 3.35 mol) is dissolved in diethoxymethane (DEM) (10 L), and D-leucine methyl ester hydrochloride (0.67 kg; 3.7 mol) is added, followed by diisopropylethylamine (0.52 kg; 4.0 mol). The resulting mixture is stirred at 20° C. for 30 min, and treated with sodium triacetoxyborohydride (0.85 kg; 4.0 mol) giving a temperature rise to 31° C. After 1 h, HPLC indicates complete consumption of the starting material. The resulting mixture is washed with water (2×7 L), and heated to reflux. Distillate (5 L) is removed, and at a pot temperature of 80 to 85° C. the reaction is held for 14 h giving complete lactamization by HPLC. The reaction mixture is cooled to 5° C., and aqueous LiOH ((0.1 kg; 4.1 mol) in 1.5 L water) and MeOH (2.0 L) are charged to the reaction. The resulting mixture is warmed to 20° C., and held for 4 h. HPLC indicates >95% conversion to compound B. The pH is adjusted to between 2 to 3 with 1N HCl and EtOAc (5 L) is charged. The aqueous layer is removed and the organic layer is washed with water (2×5 L), concentrated via distillation to 3 L. DEM (7 L) is added and the distillation is continued to remove EtOAc. The reaction volume is reduced to 6 L and cooled to 65° C. After 1 h, the resulting slurry is slowly cooled to 0° C. and held for 3 h. The solids are filtered and washed with cold DEM (1×2 L) and finally with heptane (2×3 L). The product is dried at 50° C. and 25" Hg for 48 h giving compound B (1.1 kg: 86% overall isolated yield) as a white powder.

IR (KBr pellet) 3449, 2958, 2873, 2583, 1735, 1632 cm$^{-1}$. Mixture of diastereomers: $^1$H NMR (400 MHz, CDCl$_3$) δ9.40 (1H, bs), 7.46–7.33 (5H, m), 7.22 (1H, d, J=8.6 Hz), 7.17 (1H, d, J=8.6 Hz), 6.96 (2H, d, J=8.6 Hz), 5.07 (1H, s), 5.05 (1H, s), 4.92 (1H, dd, J=8.0, 15.6 Hz), 3.75 (1H, m), 3.62 (1H, m), 3.42, (1H, m), 2.54 (1H, m), 2.12 (1H, m), 1.81 (2H, m), 1.55 (1H, m), 0.99 (6H, m). $^{13}$C NMR (100 MHz, CDCl$_3$) δ176.8, 174.7, 174.4, 157.7, 136.8, 131.9, 131.5, 129.1, 128.8, 128.4, 127.7, 127.3, 114.9, 69.8, 52.4, 47.4, 42.3, 42.0, 37.3, 36.8, 28.5, 28.3, 24.9, 23.0, 21.1, 20.9. HRMS (ESI) calcd for C$_{23}$ H$_{28}$ NO$_4$ (M$^+$) 382.201, found 382.202.

Compound C$_1$: (R)-3-aminohydroxy-1-((R)-2-amino-4-methyl-pentanoic acid)-3-(4-benzyloxy-phenyl)-pyrrolidin-2-one.

Under a nitrogen atmosphere, LiCl (30 g; 708 mmol) is charged to a vessel, followed by THF (1.05 L). The resulting mixture is stirred at 20° C. for 0.5 h at which point the mixture is almost homogeneous. Compound B (45 g; 118 mmol) is added, and the mixture cooled to –50° C. 2.5N n-Butyllithium (97.2 mL; 241.83 mmol) in hexanes is added over 0.5 h, and the resulting mixture cooled to –70° C. To the reaction mixture a 23.5 wt % solution of 1-chloro-1-nitrosocyclopentane (113.2 mL; 153.36 mmol) in methyl tert-butyl ether (MTBE) is added over 0.5 h (HPLC indicates>95% conversion and a 9:1 diastereomer ratio), followed by a THF solution of methanesulfonic acid (8 mL; 124 mmol; in 90 mL THF) over 15 min. Trimethylphosphite (12.52 mL; 106.17 mmol) is added to the reaction mixture, followed by warming to 0° C. over 0.5 h, and holding for an additional 0.5 h. An aqueous lithium hydroxide solution (4.3 g; 177 mmol; in 1.35 L of water) is added to the reaction mixture (aqueous pH>12), followed by heptane (400 mL). After vigorous mixing, the phases are separated, and the aqueous phase washed with a further 300 mL of heptane. Ethyl acetate (450 mL) is added to the aqueous phase, and the resulting mixture warmed to 30° C. with vigorous mixing. 10% Aqueous citric acid (250 mL) is added to the mixture until pH 3.6 is reached. After 0.5 h of vigorous mixing, the organic phase is separated, washed with brine (500 mL water+100 mL saturated aqueous brine), and the solvent exchanged for 2-propanol (IPA) via azeotropic distillation (final volume of 400 mL). The reaction mass is held at 60° C., and water (600 mL) is added to the mixture over 2 h inducing precipitation. The resulting slurry is cooled to 20° C. over 2 h, filtered, and washed with 40% IPA/water (2×100 mL). After drying at 70° C. and 25" Hg to constant weight, the product (32.0 g; 65% isolated yield) is afforded as a light yellow solid, as a single diastereomer. Absolute stereochemistry was confirmed by single crystal X-Ray analysis.

IR (KBr pellet) 3378, 2968, 2878, 1692 cm$^{-1}$. Single diastereomer: $^1$H NMR (400 MHz, CDCl$_3$) δ 7.61 (1H, s), 7.45–7.37 (5H, m), 7.33 (2H, d, J=8.8 Hz), 6.94 (2H, d, J=8.8 Hz), 5.09 (2H, s), 4.71 (1H, dd, J=4.0, 11.6 Hz), 3.34–3.20 (4H, m), 2.63–2.56 (1H, m), 2.13–2.09 (1H, m), 1.81–1.74 (1H, m), 1.62–1.49 (2H, m), 0.92 (3H, d, J=6.6 Hz), 0.87 (3H, d, J=6.6 Hz). $^{13}$C NMR (100 MHz, CDCl$_3$) δ174.3, 172.6, 157.6, 137.1, 132.3, 128.4, 127.9, 127.7, 127.5, 114.3, 70.5, 69.1, 51.8, 39.0, 36.3, 29.7, 24.1, 23.1, 21.0. HRMS (ESI) calcd for C$_{23}$ H$_{29}$ N$_2$O$_5$ (M$^+$) 413.209, found 413.209. [α]$_D$ (25° C.) –29.0 (c 1.064, MeOH).

Compound D from Compound C$_1$: (R)-3-amino-1-((R)-2-amino-4-methyl-pentanoic acid methyl ester)-3-(4-hydroxy-phenyl)-pyrrolidin-2-one.

Under a nitrogen atmosphere, compound C (10 g; 24.27 mmol) is suspended in MeOH (250 mL) and heated to 40° C. for 0.5 h giving a homogeneous mixture. Palladium on carbon (6.0 g; 54% wet; 8% palladium based on dry weight; 220 mg Pd; Degussa) is charged to the reaction, and the nitrogen replaced with hydrogen. The pressure is increased to 60 PSI and returned to atmospheric pressure three times, and finally held at 60 PSI. After 3.5 h, HPLC indicates complete conversion to the corresponding phenol/primary amine intermediate. The reaction mixture is cooled to 25° C., and filtered through a bed of Celite® over whatman filter paper. The clarified mixture is held at 25° C., and treated with methanesulfonic acid (3.15 mL; 48.54 mmol). After 18 h, HPLC indicates complete conversion to the title ester, compound D. The resulting mixture is neutralized with saturated aqueous sodium bicarbonate, and extracted with dichloromethane (2×500 mL). After drying the organic phase with sodium sulfate, and removing the solvent in vacuo a white solid is obtained. Drying the white solid at 50° C. and 25" Hg to constant weight affords compound D (7.0 g; 91% isolated yield). The product was recrystallized from EtOAc/heptane to give colorless needles as an EtOAc solvate.

IR (KBr pellet) 3406, 3358, 3298, 3144, 2964, 2874, 1746, 1688 cm$^{-1}$. $^1$H NMR (400 MHz, CDCl$_3$) δ 7.23 (2H, d, J=8.8 Hz), 6.62 (2H, d, J=8.8 Hz), 5.00–4.96 (1H, m, apparent J=7.6 Hz), 3.98 (3H, bs), 3.70 (3H, s), 3.38–3.29 (2H, m), 2.51–2.46 (1H, m), 2.18–2.10 (1H, m), 1.81–1.77 (2H, m, apparent J=7.6 Hz), 1.56–1.49 (1H, m), 0.99 (3H, d, J=4.5 Hz), 0.97 (3H, d, J=4.5 Hz). $^{13}$C NMR (100 MHz, CDCl$_3$) δ178.0, 171.3, 156.0, 132.5, 126.7, 115.5, 62.8, 52.4, 52.1, 39.6, 36.8, 36.6, 24.6, 23.0, 21.1. HRMS (ESI) calcd for C$_{17}$ H$_{25}$ N$_2$O$_4$ (M$^+$) 321.181, found 321.181. [α]$_D$ (25° C.) –6.4 (c 0.962, MeOH).

Compound E: (R)-3-amino-1-((R)-2-amino-4-methyl-pentanoic acid methyl ester)-3-[4-(4-methyl alcohol-2-methyl-quinoline)-phenyl]-pyrrolidin-2-one-hydrochloride-monohydrate.

Under a nitrogen atmosphere, compound D (20 g; 62.4 mmol) is dissolved in isopropyl acetate (200 mL), and p-tolualdehyde (8.2 g; 68.6 mmol) is added to the mixture. The mixture is heated to 60° C. for 1 h. A distillation head is attached and the mixture is heated to reflux to allow azeotropic removal of water. After 150 mL of distillate is removed, the reaction mixture is cooled to 60° C. and acetonitrile (150 mL) is added. 4-Chloromethyl-2-methyl-quinoline (13.1 g; 68.6 mmol), potassium carbonate (10.3 g; 74.9 mmol), and tetrabutylammonium iodide (0.9 g; 2.5 mmol) are then charged to the reaction mixture. The temperature is increased to 70° C. After 1.5 h, HPLC indicates a complete conversion to the intermediate imine. The reaction mixture is cooled to 20° C., and water (200 mL) is added. Methane sulfonic acid (13.1 g; 136 mmol) is then charged (pH 1) along with tert-butyl methyl ether (150 mL). After agitation, the layers are allowed to separate and the organic layer is discarded. Ethyl acetate (150 mL) and tert-butyl methyl ether (150 mL) are then added and the pH of the mixture is adjusted to 7 to 8 using a 50 wt % NaOH solution (10.9 g, 136 mmol). After agitation, the layers are allowed to separate and the water layer is discarded. The organic layer is then warmed to 50° C. for salt formation. 6N HCl (10.5 mL; 63 mmol) is then added over 30 min to form a slurry of the desired crystalline product. The mixture is cooled to 20° C. and held for 1 h. The product is then filtered off and washed with ethyl acetate (2×60 mL). The product is dried at 50° C. under vacuum to yield 30.0 g (91%) of the white solid.

$^1$H NMR (400 MHz, DMSO d$_6$) δ 9.27 (3H, s), 8.13 (1H, d, J=8.1 Hz), 7.98 (1H, d, J=8.1 Hz), 7.76 (1H, t, J=8.1 Hz), 7.58 (1H, s), 7.58 (2H, d, J=8.9 Hz), 7.59 (1H, t, J=7.7 Hz), 7.26 (d, 2H, J=8.9 Hz), 5.67 (s, 2H), 4.79 (dd, 1H, J$_1$=3.8 Hz, J$_2$=11.3 Hz), 3.61 (s, 3H), 3.52–3.43 (1H, m), 3.39 (2H, s) 3.15–3.25 (1H, m) 2.67 (3H, s,), 2.65–2.50 (2H, m), 1.83 (1H, t, J=10.3 Hz), 1.70–1.52 (2H, m), 0.94 (3H, d, J=6.1 Hz), 0.91 (3H, d, J=5.9 Hz). $^{13}$C NMR (100 MHz, MeOD) δ 173.4, 172.6, 160.9, 148.2, 145.6, 131.6, 129.8, 129.0, 128.8, 128.1, 125.9, 125.0, 121.9, 117.0, 68.1, 64.3, 54.5, 53.4, 41.6, 38.1, 34.1, 26.2, 25.1, 24.0, 22.0. Analysis Calculated for C$_{18}$H$_{36}$ClN$_3$O$_5$: C, 63.45; H, 6.85; Cl, 6.69; N, 7.93.

Alternate preparation of Compound E: (R)-3-amino-1-((R)-2-amino-4-methyl-pentanoic acid methyl ester)-3-[4-(4-methyl alcohol-2-methyl-quinoline)-phenyl]-pyrrolidin-2-one-hydrochloride-monohydrate.

Under a nitrogen atmosphere, compound D (10 g; 31.2 mmol), cesium carbonate (11.1 g; 34.1 mmol), 4-chloromethyl-2-methyl-quinoline (6.5 g; 34.0 mmol), tetrabutylammonium iodide (0.6 g; 1.6 mmol), and acetonitrile (100 mL) are combined. The reaction mixture is held at 20° C. for 4 h and then warmed to 40° C. After 4 h, HPLC indicates >95% of Compound D has been consumed. The mixture is cooled to 20° C. and the solids are removed by filtration. Acetonitrile (50 mL) is used to wash the cake and is combined with the original filtrate. While stirring, 6N HCl (2.2 mL, 13.2 mmol) is added dropwise to induce salt formation. Nucleation may be initiated by adding 100 mg of desired product. Once the crystallization has occurred, 6N HCl (2.3 mL, 13.8 mmol) is added dropwise over 15 min. The slurry is held for 1 to 3 h before filtering off the solid product. The white crystalline product is then washed with ethyl acetate (2×20 mL) and dried in a vacuum oven at 50° C. to a constant weight (yield 12.8 g).

Example 2

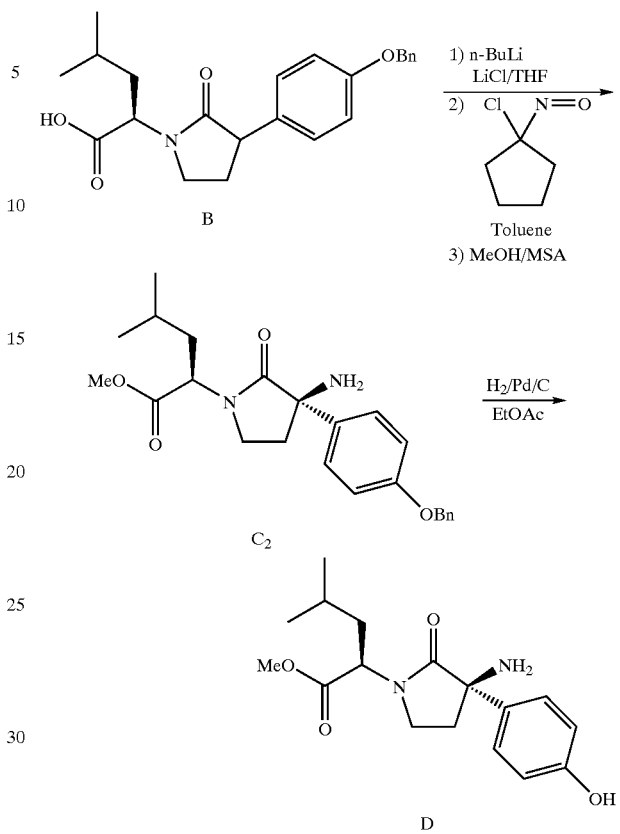

Compound C$_2$: (R)-3-amino-1-((R)-2-amino-4-methyl-pentanoic acid methyl ester)-3-(4-benzyloxy-phenyl)-pyrrolidin-2-one.

Under an N$_2$ atmosphere, Compound B (1.0 kg; 2.6 mol) and LiCl (110 g; 2.6 mol) are charged to a vessel, followed by THF (10.0 L). The resulting mixture is cooled to −70° C. 2.5N n-Butyllithium (2.6L mL; 6.5 mol.) in hexanes is added over 1 h, while maintaining a temperature below −70° C. To the reaction mixture is added a 20 wt % solution of 1-chloro-1-nitrosocyclopentane (2.3 kg; 3.1 mol) in toluene over 0.5 h, while maintaining a reaction temperature below −70° C. (HPLC indicates >97% conversion and a 11:1 diastereomer ratio). Zinc flake (1.0 kg; 15.7 mol) is added to the reaction mixture followed by neat formic acid (1.0 kg; 20.9 mol). The reaction mass is warmed to 20° C. and held there for 2 h (HPLC indicates >98% conversion). The reaction mass is filtered to remove zinc and the cake is rinsed with THF (1 L).

The filtrate is returned to the vessel and methyl alcohol (10 L) and methanesulfonic acid (1.0 kg; 10.5 mol) were added. The volume of the reaction mass was reduced (25° C. and 130 mmHg) to 10 L. The reaction mass was stirred at 20° C. until HPLC analysis indicated complete conversion (>99%). Toluene (10 L) is added to the reaction mixture followed by a solution of sodium acetate (1.8 kg in 8 L of water). The solution is stirred for 15 min and the phases separated. The organic layer is washed with a solution of sodium acetate (1.8 kg in 8 L of water), a solution of potassium bicarbonate (1.0 kg in 8 L), and water (8 L). The organic layer is concentrated under reduced pressure (27.8° C. @ 30 mmHg) to a volume of 4 L. The reaction mass is warmed to 40° C. and heptane (1 L) is added while maintaining 40° C. The solution is cooled to 20° C. over 1 h and held at 20° C. for an additional 1 h (crystallization occurs during this time). Heptane (7 L) is added and the slurry is stirred for an additional 2 h. The solution is filtered and washed with 2 L of 20% toluene/heptane. The product is dried at 50° C. and 25" Hg for 24 h giving compound C (600 g: 56% overall isolated yield) as a white to off white powder.

Single diastereomer: $^1$H NMR (400 MHz, CDCl$_3$) δ7.43 (m, 4H), 7.35(d, 2H, J=6.57 Hz), 7.28(m, 1H), 6.94(d, 2H, J=9.10 Hz), 5.03(s, 2H), 4.98(t, 1H, J=8.08 Hz), 3.65(s, 3H), 3.27(m, 2H), 2.41(m, 1H, apparent J=6.57 Hz), 2.10(m, 1H), 2.01(s, 2H), 1.77(t, 2H, J=7.58 Hz), 1.52(m, 1H, apparent J=6.57 Hz), 0.98(d, 6H, J=7.58 Hz). $^{13}$C NMR (100 MHz, CDCl$_3$) δ 178.04, 171.81, 158.31, 137.19, 135.19, 128.77, 128.13, 127.65, 127.38, 114.90, 70.11, 63.10, 52.57, 52.37, 39.60, 37.48, 37.19; 25.09, 23.47, 21.52. IR (thin film) 3364, 3037, 2948, 2871, 1729, 1684, 1610 cm$^{-1}$. MS (ESI+) 412, 394.

Compound D from Compound C2: (R)-3-amino-1-((R)-2-amino-4-methyl-pentanoic acid methyl ester)-3-(4-hydroxy-phenyl)-pyrrolidin-2-one.

Compound C (500 g; 1.22 mol) and activated carbon (100 g) are suspended in EtOAc (7.5 L) at room temperature for 0.5 h. The carbon is filtered off using a pad of Celite®. The solution is charged to an appropriate autoclave and inerted (3x) with nitrogen. Degussa-type E101 palladium on carbon (75.0 g; 50% wet; 10% palladium based on dry weight) is charged to the reactor, and the nitrogen replaced with hydrogen. The pressure is increased to 50 PSI and held at 20–30° C. and 50 PSI. After 3.5 h, HPLC indicates complete conversion (>99%). The reaction mixture is cooled to 25° C., and the catalyst is filtered off using a bag filter. The solution is concentrated to a volume of 1.5 L under reduced pressure while maintaining a maximum pot temperature of 50° C. Heptane (2 L) is added to the warm solution, and then the solution is allowed to cool to 20° C. (crystallization begins at about 30° C.). When the batch reaches 20° C., an additional charge of heptane (3 L) is added. The slurry is filtered and washed with 1 liter of a 5% EtOAc/heptane solution. The solid is dried in a vacuum oven at 50° C. overnight to give the title product (314 g; 81.2% isolated yield).

IR (KBr pellet) 3406, 3358, 3298, 3144, 2964, 2874, 1746, 1688 cm$^{-1}$. $^1$H NMR (400 MHz, CDCl$_3$) δ 7.19(d, 2H, J=8.59 Hz), 6.60(d, 2H, J=8.59 Hz), 4.90(t, 1H, J=7.58 Hz), 3.61(s, 3H), 3.25(m, 2H), 2.42(m, 1H), 2.09(m, 1H), 1.72(m, 2H), 1.45(m, 1H, apparent J=7.07 Hz), 0.89(t, 6H, J=7.07 Hz). $^{13}$C NMR (100 MHz, CDCl$_3$) δ178.32, 171.62, 156.47, 132.83, 127.03, 115.86, 63.18, 52.73, 52.48, 39.98, 37.08, 36.97, 24.97, 23.38, 21.40. MS (ESI+) 321, 304. HRMS (ESI) calcd for C$_{17}$H$_{25}$N$_2$O$_4$ (M$^+$) 321.181, found 321.181.

Example 3

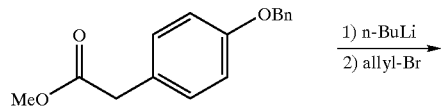

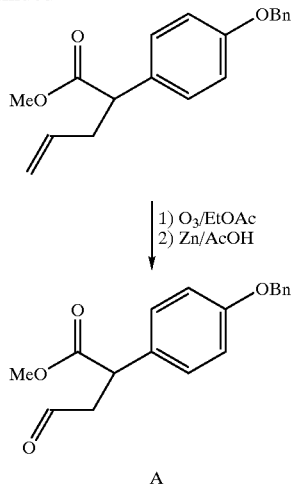

Starting Compound: 2-(4-benzyloxy-phenyl)-pent-4-enoic acid methyl ester.

To a 22 L glass flask were charged 0.35 kg (3.5 mol, 1.2 eq) of diisopropylamine and 3.75 L of tetrahydrofuran (THF). The solution was cooled to −70±5° C. and 1.29 L (3.2 mol, 1.1 eq) of 2.5 M n-butyllithium (BuLi) was charged, keeping temperature <−20° C. The reaction was warmed to −5±5° C. to allow the formation of lithium diisopropylamine (LDA). Commercial LDA in THF may be substituted for the previous procedure. The mixture was cooled −70±5° C. while 0.75 kg (2.9 mol, 1 eq) of methyl-4-benzyloxyphenylacetate was dissolved in 2.2 L of THF. The methyl-4-benzyloxyphenylacetate solution was slowly charged to the LDA solution while holding at −70±5° C. After approximately 1 h −70±5° C., during which a light green enolate slurry formed, 0.46 kg (3.8 mol, 1.3 eq) of allyl bromide was charged to the reactor. The reaction was warmed to −40±5° C. and held for about 1 h or until the reaction was deemed complete by HPLC analysis (criteria: >97% conversion of methyl-4-benzyloxyphenylacetate). An aqueous solution of dihydrogen sodium phosphate monohydrate (NaH$_2$PO$_4$) was prepared using 0.75 kg (5.4 mol, 1.9 eq) and 8 L water. The phosphate solution was added to the reaction mixture and allow to warm to 20±5° C. Ethyl acetate (EtOAc) was charged and the reaction was held for 5 min. After allowing the layers to separate, the aqueous layer was removed. The organic layer was washed two times with 6 L of water. Using vacuum distillation at <40° C., the solution was concentrated until distillation becomes difficult.

$^1$H NMR (400 MHz, CDCl$_3$) δ 7.45–7.25 (5H, m), 7.22 (2h, d, J=8.6 Hz), 6.92 (2H, J=8.6 Hz) 5.70 (1H, m), 5.06 (1H, d, J=17.1 Hz), 5.01 (2H, s), 5.01–4.96 (1H, m), 3.62 (3H, s), 3.59 (1H, t, J=8.6 Hz), 2.85–2.73 (1H, m), 2.50–2.45 (1H, m). $^{13}$C NMR (100 MHz, CDCl$_3$) δ 174.4, 158.3, 137.2, 135.6, 131.1, 129.4, 129.2 128.8, 128.2, 127.7, 117.2, 115.2, 70.2, 52.2, 50.8, 37.9.

Compound A: 2-(4-benzyloxy-phenyl)-4-oxo-butyric acid methyl ester.

7.5 L of EtOAc was added to the 2-(4-benzyloxy-phenyl)-pent-4-enoic acid methyl ester concentrate (~2.9 mol) in a 12 L flask. The reactor was cooled to −50 to −55° C. The introduction of ozone was started below the surface of the liquid with high agitation. When ozone was no longer being consumed and/or the solution turned light gray/blue a sample was submited for HPLC analysis (criteria: >99% conversion of 2-(4-benzyloxy-phenyl)-pent-4-enoic acid methyl ester). The reaction was warmed to −30±5° C. while purging with nitrogen to remove excess ozone from solution. Next, 0.75 L of acetic acid and 0.75 L of water was added. Using a powder addition funnel (screw funnel), the addition of zinc was begun (typical zinc used was ~325 mesh, 99.9% pure). The temperature was held between −10 and −20° C. during additions. The Zinc (0.37 kg, 5.6 mol, 2 eq) was added over four charges with a minimum of 20 min between additions of zinc to avoid large exotherms. After the zinc additions, the reaction was held at 0 to −10° C. for 30 min. HPLC analysis was used to determine the consumption of the ozonide (criteria: >99.8% conversion of ozonide). The contents, still at 0 to −10° C., were filtered through a 3-inch bed of Celite® (additional Celite® may be added prior to filtration) and the Celite®/Zn cake was washed with 3.0 L of EtOAc. The filtrates were combined and charged back to clean 22 L glass reactor. The ethyl acetate solution was washed two times with 4.5 L of water and 5 L of 4 wt % aqueous sodium bicarbonate (NaHCO₃). Using vacuum distillation at <30° C., the volume was reduced to approximately 3 L. 5 L of heptane was added and a sample was removed for GC analysis (criteria: <20% EtOAc by volume using GC standard). If criteria was not met, the EtOAc:Heptane ratio was adjusted by charging heptane and continuing vacuum distillation. The reaction was then cooled to 0 to 10° C. and held for a minimum of 1 h. The resulting slurry was filtered and washed with 3 L of heptane. The wet cake was dried under vacuum to afford 0.93 kg compound A (80% yield).

¹H NMR (400 MHz, CDCl₃) δ 9.69 (1H, s), 7.42–7.25 (5H, m), 7.17 (2h, d, J=8.6 Hz), 6.91 (2H, J=8.6 Hz), 4.99 (2H, s), 4.05 (1H, dd, J₁=5.1 Hz, J₂=10.1 Hz), 3.61 (3H, s), 3.31 (1H, dd, J₁=9.6 Hz, J₂=18.2 Hz), 2.72 (1H, dd, J₁=5.0, J₂=18.2 Hz). ¹³C NMR (100 MHz, CDCl₃) δ 199.6, 173.4, 158.2, 136.8, 129.9, 128.8, 128.6, 128.4, 128.0, 127.4, 127.1, 115.1, 69.9, 52.3, 47.3, 43.9.

Example 4

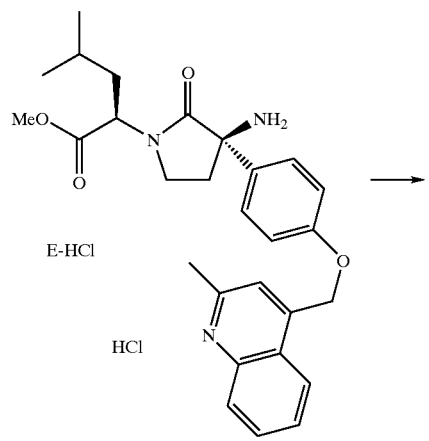

E-HCl

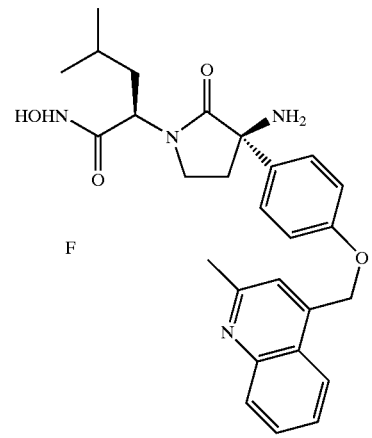

Compound F: [1(R)]-3-amino-N-hydroxy-alpha-(2-methylpropyl)-3-[4-[(2-methyl-4-quinolinyl)methoxy]phenyl]-2-oxo-1-pyrrolidineacetamide.

To a 50 gallon glass-lined reactor were charged 17.9 kg of hydroxylamine hydrochloride (257 mol, 5 eq) and 22 kg methyl alcohol. The batch temperature was set to 50° C. and 101 kg of a 25 wt % solution of sodium methoxide in methyl alcohol was charged (sodium methoxide: 25 kg, 463 mol, 9 eq) followed by a methyl alcohol rinse of the charging line. The reactor contents were heated to 55° C. and aged for 15 min. The batch was then cooled to 25° C. and filtered through a 36" nutsch filter using a polypropylene filter bag. The filtrate was collected in a 200 gallon glass-lined reactor and cooled to 10° C. 27.3 kg of Compound E-Hydrochloride ((R)-3-amino-1-((R)-2-amino-4-methyl-pentanoic acid methyl ester)-3-[4-(4-methyl alcohol-2-methyl-quinoline)-phenyl]-pyrrolidin-2-one-hydrochloride-monohydrate) (51.5 mol) was added and the batch was warmed to 25° C. for aged for 1 h. The reactor contents were sampled for reaction completion (HPLC criterion: >99.5 A % conversion). Once the reaction was deemed complete, ~70 kg of 2N HCl solution was added and the reaction mass was sampled for pH measurement (acceptance criterion: pH ~7.0). 19 L of purified water was charged and the batch was then heated to 50° C. A 1 L slurry of [1(R)]-3-amino-N-hydroxy-alpha-(2-methylpropyl)-3-[4-[(2-methyl-4-quinolinyl)methoxy]phenyl]-2-oxo-1-pyrrolidineacetamide (150 g) 1:4 methyl alcohol/water (volume ratio) was added. Purified water (126 L) was added uniformly over 1.5 h at 50° C. to induce crystallization. The batch was cooled to 5° C. over a period of 2 h. The contents were filtered and the product washed first with a mixture of methyl alcohol/water (1:4 volume ratio) and then with pure water. The wet cake (~25 kg) was analyzed to determine the weight % of water and charged to a clean 100 gallon reactor. 2-Propanol (62 kg) was added and the batch was heated to 55° C. Once all the solids were dissolved, purified water was added to adjust the volume ratio to ~55% water, 45% 2-propanol. At 55° C., 2 L slurry of milled [1(R)]-3-amino-N-hydroxy-alpha-(2-methylpropyl)-3-[4-[(2-methyl-4-quinolinyl)methoxy]phenyl]-2-oxo-1-pyrrolidineacetamide seeds (~750 g) in 1:4 2-propanol/water (volume ratio) were charged. Purified water (139 kg) was charged through a cartridge filter gradually over a period of 4.5 h. The batch was cooled from 55° C. to 20° C. in 2 h, aged for 30 min and filtered through a 36" nutsch filter using a dacron filter bag. The filter-cake was washed three times with a mixture of 2-propanol-water (1st wash: 73 kg water, 14.5 kg 2-propanol; 2nd and 3rd washes: 36 kg water, 7 kg 2-propanol). The product was dried in a tray dryer under vacuum at 50° C. to a constant weight to afford 20.9 kg compound F (81% yield).

Numerous modifications and variations of the present invention are possible in light of the above teachings. It is therefore to be understood that within the scope of the appended claims, the invention may be practiced otherwise than as specifically described herein.

What is claimed is:

1. A process of forming a compound of formula II, comprising:

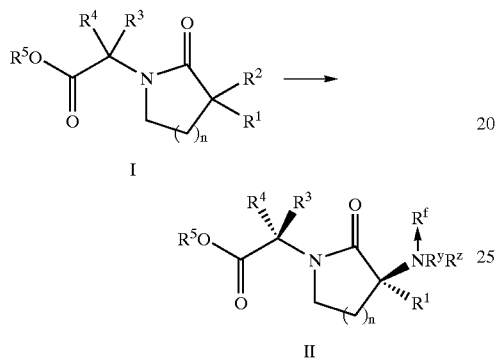

(a) contacting a compound of formula I with a strong base in the presence of a first solvent, wherein the first solvent is an aprotic solvent;
(b) contacting the resulting solution from (a) with an aminating reagent, wherein the aminating reagent is an electrophilic nitrogen source; and,
(c) if necessary, treating the amination product of (b) by reducing, hydrolyzing, or a combination thereof to form a compound of formula II;

wherein:
$R^f$ is absent;
$R^Y$ is selected from H, OH, $C_{1-6}$ alkyl, and $C_{3-12}$ cycloalkyl;
$R^z$ is selected from H, $C_{1-6}$ alkyl, and $C_{3-12}$ cycloalkyl;
alternatively, $R^f$ is O, $R^z$ is absent, and $R^y$ forms a $C_{3-12}$ cycloalkyl group double bonded to the nitrone nitrogen or is a carbon atom double bonded to the nitrone nitrogen and substituted with $R^6$ and $R^7$;
$R^6$ is $C_{1-6}$ alkyl or $C_{3-12}$ cycloalkyl;
$R^7$ is $C_{1-6}$ alkyl or $C_{3-12}$ cycloalkyl;
$R^1$ is Z—$U^a$—$X^a$—$Y^a$—$Z^a$;
Z is phenyl
$U^a$ is absent or is O;
$X^a$ is absent or is selected from $C_{1-10}$ alkylene, $C_{2-10}$ alkenylene, and $C_{2-10}$ alkynylene;
$Y^a$ is absent or is O;
$Z^a$ is H;
$R^2$ is H;
$R^3$ is selected from H, Q, $C_{1-10}$ alkylene-Q, $C_{2-10}$ alkenylene-Q, and $C_{2-10}$ alkynylene-Q;
Q is H;
R, at each occurrence, is independently selected from H, $CH_3$, $CH_2CH_3$, $CH=CH_2$, $CH=CHCH_3$, and $CH_2CH=CH_2$;

$R^4$ is selected from H, $C_{1-10}$ alkylene-H, $C_{2-10}$ alkenylene-H, and $C_{2-10}$ alkynylene-H;
$R^5$ is selected from H, $C_{1-6}$ alkyl, phenyl, and benzyl;
n is 1.

2. A process according to claim 1, wherein (c) is performed by reducing the amination product from (b) to form a compound of formula II, wherein:
$R^y$ is selected from H, $C_{1-6}$ alkyl, and $C_{3-12}$ cycloalkyl; and,
$R^z$ is selected from H, $C_{1-6}$ alkyl, and $C_{3-12}$ cycloalkyl.

3. A process according to claim 1, wherein (a) is performed in the presence of an inorganic salt selected from a lithium salt, a potassium salt, and a sodium salt; and (c) is performed by contacting the amination product from (b) with a reducing agent and an acid;
the compound of formula I is the compound of formula Ia:

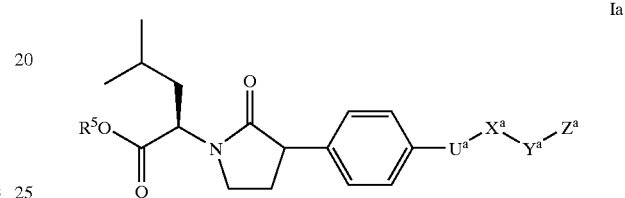

the compound of formula II is a compound of formula IIa:

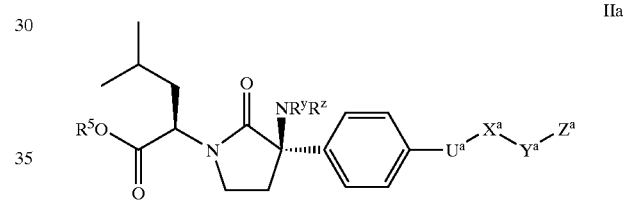

the strong base is selected from an alkyl lithium, lithium amide, hydride base, and an organometallic base;
the first solvent is selected from an ethereal solvent, a hydrocarbon solvent, and an aromatic hydrocarbon solvent;
the aminating reagent is selected from a chloro-nitroso compound, a sulfonyl azide, a nitroso compound, an azodicarboxylate, a sulfonamide, and an oxaziridine compound;
the reducing agent is selected from zinc and iron;
the acid is selected from formic acid, acetic acid, and methanesulfonic acid;
wherein:
$R^y$ is H;
$R^z$ is H;
$U^a$ is absent or is O;
$X^a$ is absent or is $C_{1-4}$ alkylene;
$Y^a$ is absent;
$Z^a$ is H;
$R^5$ is H or $C_{1-6}$ alkyl.

4. A process according to claim 3, wherein (b) is performed in the presence of a second solvent and the second solvent is an aprotic solvent;
the inorganic salt is selected from lithium chloride, lithium perchlorate, lithium bromide, lithium iodide, potassium chloride, potassium bromide, potassium iodide, sodium chloride, sodium bromide, and sodium iodide;

the strong base is selected from methyl lithium, ethyl lithium, n-propyl lithium, i-propyl lithium, n-butyl lithium, i-butyl lithium, s-butyl lithium, t-butyl lithium, hexyl lithium, lithium bis(trimethylsilyl)amide, lithium diisopropylamide, lithium 2,2,6,6-tetramethylpiperidine, potassium bis(trimethylsilyl) amide, potassium hydride, and sodium hydride;

the first solvent is selected from tetrahydrofuran, 1,2-dimethoxyethane, t-butylmethyl ether, diethyl ether, and dimethoxymethane;

the second solvent is selected from tetrahydrofuran, 1,2-dimethoxyethane, t-butylmethyl ether, diethyl ether, dimethoxymethane, and toluene;

the aminating reagent is selected from 1-chloro-1-nitrosocyclopentane, 1-chloro-1-nitrosocyclohexane, and 2-chloro-2-nitrosopropane;

the reducing agent is zinc;

wherein:

$U^a$ is O;

$X^a$ is absent or is $CH_2$;

$Z^a$ is H; and, $R^5$ is H or $CH_3$.

5. A process according to claim 4, wherein:

the inorganic salt is selected from lithium chloride and lithium perchlorate;

the strong base is selected from n-butyl lithium and hexyl lithium;

the first solvent is selected from tetrahydrofuran and 1,2-dimethoxyethane;

the second solvent is toluene; and, the aminating reagent is selected from 1-chloro-1-nitrosocyclopentane and 1-chloro-1-nitrosocyclohexane.

6. A process according to claim 5, wherein:

the inorganic salt is lithium chloride;

the strong base is n-butyl lithium;

the first solvent is tetrahydrofuran;

the second solvent is toluene;

the aminating reagent is 1-chloro-1-nitrosocyclopentane; and, the acid is formic acid.

7. A process according to claim 2, wherein (c) further comprises:

($c_1$) esterifying the acid product from $b_1$, wherein: $R^5$ is $C_{1-6}$ alkyl.

8. A process according to claim 7, wherein in ($c_1$) the esterification is performed by contacting the reduced product with an acid in the presence of an alcohol.

9. A process according to claim 8, wherein the acid is methanesulfonic acid and the alcohol is methyl alcohol.

10. A process according to claim 2, further comprising:

(d) subjecting the compound from (c) wherein $R^y$ is OH to catalytic hydrogenation with a noble metal catalyst to form a compound of formula II wherein $R^y$ is H.

11. A process according to claim 10, wherein the noble metal catalyst is palladium.

12. A compound of formula IId:

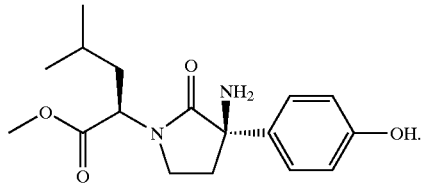

* * * * *

UNITED STATES PATENT AND TRADEMARK OFFICE
CERTIFICATE OF CORRECTION

PATENT NO. : 6,770,763 B2
DATED : August 3, 2004
INVENTOR(S) : Magnus et al.

Page 1 of 1

It is certified that error appears in the above-identified patent and that said Letters Patent is hereby corrected as shown below:

<u>Title page</u>,
Item [75], Inventors, should read -- Nicholas A. Magnus, Indianapolis, IN (US); Pasquale N. Confalone, Greenville, DE (US); Scott A. Savage, Yardley, PA (US); Matthew Yates, Lafayette, IN (US); Robert E. Waltermire, Hillsborough, NJ (US); David J. Meloni, Bear, DE (US); Silvio Campagna, Candia, NH (US) --.

Signed and Sealed this

Sixteenth Day of May, 2006

JON W. DUDAS
*Director of the United States Patent and Trademark Office*